United States Patent
Kaemmerer

(10) Patent No.: US 7,819,842 B2
(45) Date of Patent: Oct. 26, 2010

(54) CHRONICALLY IMPLANTABLE GUIDE TUBE FOR REPEATED INTERMITTENT DELIVERY OF MATERIALS OR FLUIDS TO TARGETED TISSUE SITES

(75) Inventor: William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 467 days.

(21) Appl. No.: 11/562,304

(22) Filed: Nov. 21, 2006

(65) Prior Publication Data

US 2008/0119789 A1    May 22, 2008

(51) Int. Cl.
*A61M 5/00*    (2006.01)
(52) U.S. Cl. .................................... 604/117; 600/429
(58) Field of Classification Search ............ 604/116, 604/117, 158, 159, 160, 161, 162, 164.01, 604/192, 264, 272; 606/108, 184
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,716,901 A * | 1/1988 | Jackson et al. | 606/185 |
| 4,800,159 A | 1/1989 | Mullis et al. | |
| 4,888,829 A | 12/1989 | Kleinerman et al. | |
| 4,903,707 A * | 2/1990 | Knute et al. | 600/561 |
| 4,965,188 A | 10/1990 | Mullis et al. | |
| 5,236,908 A | 8/1993 | Gruber et al. | |
| 5,354,326 A | 10/1994 | Comben et al. | |
| 5,534,350 A | 7/1996 | Liou | |
| 5,624,803 A | 4/1997 | Noonberg et al. | |
| 5,639,275 A | 6/1997 | Baetge et al. | |
| 5,702,716 A | 12/1997 | Dunn et al. | |

(Continued)

FOREIGN PATENT DOCUMENTS

DE    19938960    2/2001

(Continued)

OTHER PUBLICATIONS

Aebisher, Trends in Neurosci. 24(9) 553-540 (Sep. 2001).

(Continued)

*Primary Examiner*—Nicholas D Lucchesi
*Assistant Examiner*—Gerald Landry, II
(74) *Attorney, Agent, or Firm*—Kenneth J. Collier; Gerard P. Norton; Fox Rothschild LLP

(57) ABSTRACT

A therapy delivery system for the intermittent delivery of biologics, chemicals, or pharmaceuticals into tissues involves a chronically implantable guide tube having a guide cannula with a proximal and a distal end, an access port mounted on the proximal end of the guide cannula and adapted for chronic implantation into a patient, a first stop mounted near the distal end of the guide cannula and a delivery cannula insertable into the lumen of the guide cannula through the access port. The delivery cannula mechanically interacts with the first stop and is designed to prevent the delivery cannula from extending beyond a predetermined distance from the distal end of the guide cannula. A tissue-piercing tip may be attached to the distal end of the delivery cannula. A stylet may be used to occupy the lumen of the guide cannula when the delivery cannula is not in use.

23 Claims, 3 Drawing Sheets

U.S. PATENT DOCUMENTS

| | | | |
|---|---|---|---|
| 5,720,720 A | 2/1998 | Laske et al. | |
| 5,735,814 A | 4/1998 | Elsberry et al. | |
| 5,782,892 A | 7/1998 | Castle et al. | |
| 5,800,390 A | 9/1998 | Hayakawa et al. | |
| 5,814,014 A | 9/1998 | Elsberry et al. | |
| 5,840,059 A | 11/1998 | March et al. | |
| 5,882,561 A | 3/1999 | Barsoum et al. | |
| 5,925,310 A | 7/1999 | Nakayama et al. | |
| 5,942,455 A | 8/1999 | Barsoum et al. | |
| 5,968,059 A | 10/1999 | Ellis et al. | |
| 5,997,525 A | 12/1999 | March et al. | |
| 6,042,579 A | 3/2000 | Elsberry et al. | |
| 6,093,180 A | 7/2000 | Elsberry | |
| 6,110,459 A | 8/2000 | Mickle et al. | |
| 6,151,525 A | 11/2000 | Soykan et al. | |
| 6,179,826 B1 * | 1/2001 | Aebischer et al. | 604/522 |
| 6,180,613 B1 | 1/2001 | Kaplitt et al. | |
| 6,187,906 B1 | 2/2001 | Gluckman et al. | |
| 6,231,969 B1 | 5/2001 | Knight et al. | |
| 6,245,884 B1 | 6/2001 | Hook | |
| 6,281,009 B1 | 8/2001 | Boyce | |
| 6,291,243 B1 | 9/2001 | Fogarty et al. | |
| 6,294,202 B1 | 9/2001 | Burns et al. | |
| 6,300,539 B1 | 10/2001 | Morris | |
| 6,309,634 B1 | 10/2001 | Bankiewicz et al. | |
| 6,310,048 B1 | 10/2001 | Kumar | |
| 6,313,268 B1 | 11/2001 | Hook | |
| 6,319,905 B1 | 11/2001 | Mandel et al. | |
| 6,343,233 B1 | 1/2002 | Werner et al. | |
| 6,372,250 B1 | 4/2002 | Pardridge | |
| 6,372,721 B1 | 4/2002 | Neuman et al. | |
| 6,376,471 B1 | 4/2002 | Lawrence, III et al. | |
| 6,436,392 B1 | 8/2002 | Engelhardt et al. | |
| 6,436,708 B1 | 8/2002 | Leone et al. | |
| 6,461,989 B1 | 10/2002 | El-Raghy et al. | |
| 6,468,524 B1 | 10/2002 | Chiorini et al. | |
| 6,551,290 B1 | 4/2003 | Elsberry et al. | |
| 6,594,880 B2 | 7/2003 | Elsberry | |
| 6,609,020 B2 | 8/2003 | Gill | |
| 6,632,671 B2 | 10/2003 | Unger | |
| 6,659,995 B1 | 12/2003 | Taheri | |
| 6,870,030 B2 | 3/2005 | Powell et al. | |
| 6,945,969 B1 | 9/2005 | Morris et al. | |
| 7,255,686 B2 * | 8/2007 | Putz | 604/164.09 |
| 7,320,965 B2 | 1/2008 | Sah et al. | |
| 2001/0003156 A1 | 6/2001 | Gill | |
| 2001/0027309 A1 | 10/2001 | Elsberry | |
| 2001/0031947 A1 | 10/2001 | Heruth | |
| 2002/0004038 A1 | 1/2002 | Baugh et al. | |
| 2002/0068093 A1 | 6/2002 | Trogolo et al. | |
| 2002/0114780 A1 | 8/2002 | Bankiewicz | |
| 2002/0141980 A1 | 10/2002 | Bankiewicz | |
| 2002/0187127 A1 | 12/2002 | Bankiewicz | |
| 2003/0078229 A1 | 4/2003 | Cooper et al. | |
| 2003/0088236 A1 | 5/2003 | Johnson et al. | |
| 2003/0092003 A1 | 5/2003 | Blatt et al. | |
| 2003/0095958 A1 | 5/2003 | Bhisetti et al. | |
| 2003/0109476 A1 | 6/2003 | Kmiec et al. | |
| 2003/0120282 A1 | 6/2003 | Scouten et al. | |
| 2003/0143732 A1 | 7/2003 | Fosnaugh et al. | |
| 2003/0152947 A1 | 8/2003 | Crossman | |
| 2003/0175772 A1 | 9/2003 | Wang | |
| 2003/0187320 A1 * | 10/2003 | Freyman | 600/13 |
| 2003/0190635 A1 | 10/2003 | McSwiggen | |
| 2003/0224512 A1 | 12/2003 | Dobie | |
| 2004/0018520 A1 | 1/2004 | Thompson | |
| 2004/0023390 A1 | 2/2004 | Davidson | |
| 2004/0023855 A1 | 2/2004 | John et al. | |
| 2004/0162531 A1 * | 8/2004 | Wenchell | 604/264 |
| 2004/0186422 A1 | 9/2004 | Rioux | |
| 2004/0193114 A1 * | 9/2004 | Elbert et al. | 604/164.1 |
| 2004/0215164 A1 | 10/2004 | Abbott | |
| 2004/0220132 A1 | 11/2004 | Kaemmerer | |
| 2004/0258666 A1 | 12/2004 | Passini | |
| 2004/0259247 A1 | 12/2004 | Tuschl | |
| 2004/0265849 A1 | 12/2004 | Cargill | |
| 2004/0266707 A1 | 12/2004 | Leake | |
| 2005/0032733 A1 | 2/2005 | McSwiggen | |
| 2005/0042646 A1 | 2/2005 | Davidson | |
| 2005/0048641 A1 | 3/2005 | Hildebrand | |
| 2005/0096284 A1 | 5/2005 | McSwiggen | |
| 2005/0137134 A1 | 6/2005 | Gill | |
| 2005/0153353 A1 | 7/2005 | Meibohm | |
| 2005/0180955 A1 | 8/2005 | Bankiewicz | |
| 2005/0202075 A1 | 9/2005 | Pardridge | |
| 2005/0209179 A1 | 9/2005 | McSwiggen | |
| 2005/0255086 A1 | 11/2005 | Davidson | |
| 2005/0282198 A1 | 12/2005 | Duff | |
| 2006/0009408 A1 | 1/2006 | Davidson et al. | |
| 2006/0014165 A1 | 1/2006 | Hackonarson | |
| 2006/0041242 A1 | 2/2006 | Stypulkowski | |
| 2006/0150747 A1 | 7/2006 | Mallett | |
| 2006/0183698 A1 * | 8/2006 | Abelson | 514/35 |
| 2006/0210538 A1 | 9/2006 | Kaplitt et al. | |
| 2006/0224111 A1 | 10/2006 | Rosenman et al. | |
| 2006/0224411 A1 | 10/2006 | Chang | |
| 2006/0257912 A1 | 11/2006 | Kaemmerer | |
| 2007/0031844 A1 | 2/2007 | Khvorova et al. | |
| 2007/0184029 A1 | 8/2007 | Mishra | |
| 2008/0109026 A1 * | 5/2008 | Kassam | 606/190 |
| 2008/0113351 A1 | 5/2008 | Naito | |
| 2009/0022864 A1 | 1/2009 | Steenhof | |

FOREIGN PATENT DOCUMENTS

| | | |
|---|---|---|
| JP | 2004232811 | 8/2004 |
| WO | WO92/20400 | 11/1992 |
| WO | WO 92/20400 | 11/1992 |
| WO | WO9220400 | 11/1992 |
| WO | WO9323569 | 11/1993 |
| WO | WO9402595 | 2/1994 |
| WO | WO9618736 | 6/1996 |
| WO | WO9740847 | 11/1997 |
| WO | WO9846273 | 10/1998 |
| WO | WO9846740 | 10/1998 |
| WO | WO9939744 | 8/1999 |
| WO | WO9950300 | 10/1999 |
| WO | WO0030567 | 6/2000 |
| WO | WO 0064505 | 11/2000 |
| WO | WO0116312 | 3/2001 |
| WO | WO0149844 | 7/2001 |
| WO | WO0160794 | 8/2001 |
| WO | WO0170276 | 9/2001 |
| WO | WO0180840 | 11/2001 |
| WO | WO0191801 | 12/2001 |
| WO | WO0205804 | 1/2002 |
| WO | WO0207810 | 1/2002 |
| WO | WO0222177 | 3/2002 |
| WO | WO03042385 | 5/2003 |
| WO | WO03047676 | 6/2003 |
| WO | WO03053516 | 7/2003 |
| WO | WO03070895 | 8/2003 |
| WO | WO03099298 | 12/2003 |
| WO | WO03102131 | 12/2003 |
| WO | WO2004007718 | 1/2004 |
| WO | WO2004010787 | 2/2004 |
| WO | WO2004013280 | 2/2004 |
| WO | WO2004013355 | 2/2004 |
| WO | WO2004041101 | 5/2004 |
| WO | WO2004047872 | 6/2004 |
| WO | WO2004058940 | 7/2004 |
| WO | WO2004084955 | 10/2004 |
| WO | WO2004098648 | 11/2004 |
| WO | WO2004101063 | 11/2004 |

| WO | WO2005027980 | 3/2005 |
| WO | WO2005045034 | 5/2005 |
| WO | WO2005116204 | 8/2005 |
| WO | WO2005120581 | 12/2005 |
| WO | WO2006022639 | 3/2006 |
| WO | WO2007039721 | 4/2007 |
| WO | WO2008005562 | 7/2007 |
| WO | WO2007087451 | 8/2007 |
| WO | WO2007139811 | 12/2007 |
| WO | WO2008004260 | 1/2008 |
| WO | WO2008021157 | 2/2008 |
| WO | WO2008046273 | 4/2008 |
| WO | WO2008143774 | 11/2008 |

OTHER PUBLICATIONS

Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 μg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.
Basi et al., "Antagonistic Effects of β-site Amyloid Precursor Protein-cleaving Enzymes 1 and 2 on β- Amyloid Peptide Production in Cells," J. Bio. Chem., Published, JBC Papers in Press, Jun. 2003; 278(34): 31512-31520.
Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillee et al., "Gene therapy for ALS deliver," Trends in Neurosciences, May 2004; 27(5): 235-238.
Bortolin, Susan et al., "Analytical validation of the tag-it high-throughput microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100(11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; 12(12): 1587-1598.
ElBashir, EMBOJ 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behav. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid. Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes," Proc. Natl. Acad., USA, Nov. 1996;93:14164-14169.
Invitrogen, pShooter™ Vector (pCMV/myc© vectors), For the intracellular targeting of recombinant proteins and antibodies, Catalog Nos. V820-20, V821-20, V822-20, V823-20, Version E, copyright 1998-2001, 35 pgs.
Invitrogen, pTRACER™ -CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Liszewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.

Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet: <URL:http://www.ncbi.nlm.nih.gov>; 2 pgs.
National Center for Biotechnology Information, National Library of Medicine, National Institutes of Health, GenBank Locus AF163864, Accession No. AF163864, "*Homo sapiens* SNCA isoform (SNCA) gene, complete cds, alternatively spliced," [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.
National Center for Biotechnology Information, National Library of Medicine, National Institutes of Health, GenBank Locus AF163865, Accession No. AF163865, "Mus musculus alpha-synuclein (SNCA) gene, complete cds," [online]. Bethesda, MD [retrieved on Jun. 21, 2004]. Retrieved from the Internet<URL:http://www.ncbi.nlm.nih.gov/entrez/viewer.fcgi?db=nucleotide&val=11118354>; 33 pgs.
National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on Mar. 5, 2009]. Retrieved from the Internet:<URL:http://www.ncbi.nlm.nih.gov/entrez/viewer.fcgi?db=nucleotide&val=663286>; 42 pgs.
National Center for Biotechnology Information, National Library of Medicine, National Institutes of Health, GenBank Locus NM_000027, Accession No. NM_000027, "*Homo sapiens* aspartylglucosaminidase (AGA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=32313568>; 4 pgs.
National Center for Biotechnology Information, National Library of Medicine, National Institutes of Health, GenBank Locus NM_000046, Accession No. NM_000046, "*Homo sapiens* arylsulfatase B (ARSB), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=38569404>; 4 pgs.
National Center for Biotechnology Information, National Library of Medicine, National Institutes of Health, GenBank Locus NM_000049, Accession No. NM_000049, "*Homo sapiens* aspartoacylase (aminoacylase 1, Canavan disease) (ASPA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557334>; 4 pgs.
National Center for Biotechnology Information, National Library of Medicine, National Institutes of Health, GenBank Locus NM_000147, Accession No. NM_000147, "*Homo sapiens* fucosidase, alpha-L1, tissue (FUCA1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=24475878>; 3 pgs.
National Center for Biotechnology Information, National Library of Medicine, National Institutes of Health, GenBank Locus NM_000152, Accession No. NM_000152, "*Homo sapiens* glucosidase, alpha; acid (Pompe disease, glycogen storage disease type II) (GAA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=11496988>; 4 pgs.
National Center for Biotechnology Information, National Library of Medicine, National Institutes of Health, GenBank Locus NM_000153, Accession No. NM_000153, "*Homo sapiens* galactosylceramidase (Krabbe disease) (GALC), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557612>; 5 pgs.
National Center for Biotechnology Information, National Library of Medicine, National Institutes of Health, GenBank Locus NM_000157, Accession No. NM_000157, "*Homo sapiens* glucosidase, beta; acid (includes glucosylceramidase) (GBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4503934>; 7 pgs.
National Center for Biotechnology Information, National Library of Medicine, National Institutes of Health, GenBank Locus NM_000158, Accession No. NM_000158, "*Homo sapiens* glucan (1, 4-alpha-), branching enzyme 1 (glucogen branching enzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557618>; 2 pgs.
National Center for Biotechnology Information, National Library of Medicine, National Institutes of Health, GenBank Locus NM_000181, Accession No. NM_000181, "*Homo sapiens* glucuronidase, beta (GUSB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504222>; 4 pgs.
National Center for Biotechnology Information, National Library of Medicine, National Institutes of Health, GenBank Locus NM_000199, Accession No. NM_000199, "*Homo sapiens* N-sulfoglucosamine sulfohydrolase (sulfamidase) (SGSH), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=31543619>; 3 pgs.
National Center for Biotechnology Information, National Library of Medicine, National Institutes of Health, GenBank Locus NM_000202, Accession No. NM_000202, "*Homo sapiens* iduronate 2-sulfatase (Hunter syndrome)(ID), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=5360215>; 8 pgs.
National Center for Biotechnology Information, National Library of Medicine, National Institutes of Health, GenBank Locus NM_000203, Accession No. NM_000203, "*Homo sapiens* iduronidase, alpha-L-(IDUA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40354208>; 6 pgs.
National Center for Biotechnology Information, National Library of Medicine, National Institutes of Health, GenBank Locus NM_000235, Accession No. NM_000235, "*Homo sapiens* lipase A, lysosomal acid, cholesterol esterase (Wolman disease) (LIPA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4557720>; 4 pgs.
National Center for Biotechnology Information, National Library of Medicine, National Institutes of Health, GenBank Locus NM_000262, Accession No. NM_000262, "*Homo sapiens* N-acetylgalactosaminidase, alpha- (NAGA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557780>; 4 pgs.
National Center for Biotechnology Information, National Library of Medicine, National Institutes of Health, GenBank Locus NM_000263, Accession No. NM_000263, "*Homo sapiens* N-acetylglucosaminidase, alpha-(Sanfilippo disease)(IIIB)(NAGLU), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=40548380>; 4 pgs.
National Center for Biotechnology Information, National Library of Medicine, National Institutes of Health, GenBank Locus NM_000310, Accession No. NM_000310, "*Homo sapiens* palmitoyl-protein thioesterase 1 (ceroid-lipofuscinosis, neuronal 1, infantile) (PPT1), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4506030>; 4 pgs.
National Center for Biotechnology Information, National Library of Medicine, National Institutes of Health, GenBank Locus NM_000332, Accession No. NM_000332, "*Homo sapiens* spinocerebellar ataxia 1 (olivopontocerebellar ataxia 1, autosomal dominant, ataxin 1) (SCA1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4506792>; 7 pgs.

National Center for Biotechnology Information, National Library of Medicine, National Institutes of Health, GenBank Locus NM_000345, Accession No. NM_000345, "*Homo sapiens* synuclein, alpha (nonA4 component of amyloid precursor) (SNCA), transcript variant NACP140, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=6806896>; 6 pgs.

National Center for Biotechnology Information, National Library of Medicine, National Institutes of Health, GenBank Locus NM_000404, Accession No. NM_000404, "*Homo sapiens* glactosidase, beta 1 (GLB1), transcript variant 179423, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834965>; 5 pgs.

National Center for Biotechnology Information, National Library of Medicine, National Institutes of Health, GenBank Locus NM_000434, Accession No. NM_000434, "*Homo sapiens* sialidase 1 (lysosomal sialidase)(NEU1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40806202>; 5 pgs.

National Center for Biotechnology Information, National Library of Medicine, National Institutes of Health, GenBank Locus NM_000487, Accession No. NM_000487, "*Homo sapiens* arysulfatase A (ARSA), mRNA," [online]. Bethesda, MD [retrieved on Mar. 5, 2009]. Retrieved from the Internet<URL:http://www.ncbi.nlm.nih.gov/entrez/viewer.fcgi? db=nucleotide&val=7262293>; 4 pgs.

National Center for Biotechnology Information, National Library of Medicine, National Institutes of Health, GenBank Locus NM_000512, Accession No. NM_000512, "*Homo sapiens* galactosamine (N-acetyl)-6-sulfate sulfatase (Morquio syndrome, mucopolysaccharidosis type IVA), (GALNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=9945384>; 4 pgs.

National Center for Biotechnology Information, National Library of Medicine, National Institutes of Health, GenBank Locus NM_000520, Accession No. NM_000520, "*Homo sapiens* hexosaminidase A (alpha polypeptide) (HEXA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13128865>; 5 pgs.

National Center for Biotechnology Information, National Library of Medicine, National Institutes of Health, GenBank Locus NM_000521, Accession No. NM_000521, "*Homo sapiens* hexosaminidase B (beta polypeptide) (HEXB), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13128866>; 6 pgs.

National Center for Biotechnology Information, National Library of Medicine, National Institutes of Health, GenBank Locus NM_000528, Accession No. NM_000528, "*Homo sapiens* mannosidase, alpha, class 2B, member 1 (MAN2B1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "*Homo sapiens* sphingomyelin phosphodiesterase 1 acid lysosomal (acid sphingomyelinase) (SMPD1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=40254417>; 5 pgs.

National Center for Biotechnology Information, National Library of Medicine, National Institutes of Health, GenBank Locus NM_002076, Accession No. NM_002076, "*Homo sapiens* glucosamine (N-acetyl)-6-sulfatase (Sanfilippo disease)(IIID)(GNS), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, "*Homo sapiens* NM_000169, "*Homo sapiens* glactosidase, alpha (GLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504008>; 4 pgs.

National Center for Biotechnology Information, National Library of Medicine, National Institutes of Health, GenBank Locus NM_002778, Accession No. NM_002778, "*Homo sapiens* prosaposin (variant Gaucher disease and variant metachromatic leukodystrophy) (PSAP), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=11386146>; 8 pgs.

National Center for Biotechnology Information, National Library of Medicine, National Institutes of Health, GenBank Locus NM_004315, Accession No. NM_004315, "*Homo sapiens* N-acylsphingosine amidohydrolase (acid ceramidase) 1 (ASAHI), transcript variant 2, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=30089929>; 5 pgs.

National Center for Biotechnology Information, National Library of Medicine, National Institutes of Health, GenBank Locus NM_004993, Accession No. NM_004993, "*Homo sapiens* Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi? db=nucleotide&val=13518018>; 9 pgs.

National Center for Biotechnology Information, National Library of Medicine, National Institutes of Health, GenBank Locus NM_005908, Accession No. NM_005908, "*Homo sapiens* mannosidase, beta A, lyosomal (MANBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus NM_007308, Accession No. NM_007308, "*Homo sapiens* synuclein, alpha (nonA4 component of amyloid precursor) (SNCA), transcript variant NACP112, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "Definition," [online]. Bethesda, MD [retrieved on Mar. 5, 2009]. Retrieved from the Internet<URL:http://www.ncbi.nlm.nih.gov/entrez/viewer.fcgi?db=nucleotide&val=33636695>; 5 pgs.

National Center for Biotechnology Information, National Library of Medicine, National Institutes of Health, GenBank Locus NM_011792, Accession No. NM_011792, Version NM_011792.2, "Mus musculus beta-site APP-cleaving enzyme 1 (Bace 1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "Mus musculus beta-site APP-cleaving enzyme (Bace), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "*Homo sapiens* beta-site APP-cleaving enzyme 1 (BACE1), transcript variant a, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "*Homo sapiens* beta-site APP-cleaving enzyme (BACE), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040369>; 10 pgs.

National Center for Biotechnology Information, National Library of Medicine, National Institutes of Health, GenBank Locus NM_013995, Accession No. NM_013995, "*Homo sapiens* lysosomal-associated membrane protein 2 (LAMP2), transcript variant LAMP2B, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=7669502>; 6 pgs.

National Center for Biotechnology Information, National Library of Medicine, National Institutes of Health, GenBank Locus NM_030660, Accession No. NM_030660, "*Homo sapiens* Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "*Homo sapiens* N-acetylglucosamine-1-phosphotransferase, gamma subunit (GNPTAG), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "*Homo sapiens* beta-site APP-cleaving enzyme 1 (BACE1), transcript variant c, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255012>; 8 pgs.

National Center for Biotechnology Information, National Library of Medicine, National Institutes of Health, GenBank Locus NM_138971, Accession No. NM_138971, Version NM_138971.1, "*Homo sapiens* beta-site APP-cleaving enzyme (BACE), transcript variant c, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040363>; 10 pgs.

National Center for Biotechnology Information, National Library of Medicine, National Institutes of Health, GenBank Locus NM_138972, Accession No. NM_138972, "*Homo sapiens* beta-site APP-cleaving enzyme 1 (BACE1), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255013>; 8 pgs.

National Center for Biotechnology Information, National Library of Medicine, National Institutes of Health, GenBank Locus NM_138972, Accession No. NM_138972, Version NM_138972.1, "*Homo sapiens* beta-site APP-cleaving enzyme (BACE), transcript variant b, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040365>; 10 pgs.

National Center for Biotechnology Information, National Library of Medicine, National Institutes of Health, GenBank Locus NM_138973, Accession No. NM_138973, "*Homo sapiens* beta-site APP-cleaving enzyme 1 (BACE1), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255014>; 8 pgs.

National Center for Biotechnology Information, National Library of Medicine, National Institutes of Health, GenBank Locus NM_138973, Accession No. NM_138973, Version NM_138973.1, "*Homo sapiens* beta-site APP-cleaving enzyme (BACE), transcript variant d, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040367>; 10 pgs.

National Center for Biotechnology Information, National Library of Medicine, National Institutes of Health, GenBank Locus U24233, Accession No. U24233, "Mus musculus huntingtin (Hd) mRNA, complete cds," [online]. Bethesda, MD [retrieved on Mar. 5, 2009]. Retrieved from the Internet:<URL:http://www.ncbi.nlm.nih.gov/entrez/viewer.fcgi?db=nucleotide&val=902003>; 5 pgs.

National Center for Biotechnology Information, National Library of Medicine, National Institutes of Health, GenBank Locus XM_032588, Accession No. XM_032588, "*Homo sapiens* dentatorubral-pallidoluysian atrophy (artrophin-1) (DRPLA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=20555988>; 3 pgs.

National Center for Biotechnology Information, National Library of Medicine, National Institutes of Health, GenBank Locus XM_132846, Accession No. XM_132846, "Mus musculus dentatorubral pallidoluysian atrophy (Drpla) mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=20832263>; 3 pgs.

Noonberg et al., Nucl. Acid Res. 22(14) 2830-2836 (1994).

Noordmans et al., Soc. Neurosci. Abstr. 27, Program 572.14 (2001).

Ohkawa Nucl. Acid. Symp. Ser. 27, 15-16 (1992).

Ohno et al., "BACE1 Deficiency Rescues Memory Deficits and Cholinergic Dysfunction in a Mouse Model of Alzheimer's Disease," Neuron, Jan. 2004; 41: 27-33.

Ojwang et al., Proc. Nat. Acad. Sci. 89 10802-10806.

Paxinos et al The Mouse Brain in Stereographic Coordinates, Acad. Press 2nd Ed. (2001).

Potter, N. T. et al., "Technical standards and guidelines for huntington disease testing," Genetics in Medicine 6:61-65 (2004).

Promega Corporation, T4 DNA Ligase Blue/White Cloning Qualified, Part# 9PIM180, Revised Apr. 2005, 2 pgs.

Promega Corporation, T4 DNA Polymerase(a) , Part# 9PIM421, Revised May 2004, 2 pgs.

Qiagen, Qiaex II Handbook, Feb. 1999, 24 pgs.

Qiagen, Rneasy Mini Handbook, 3rd Edition, Jun. 2001, 116 pgs.

R&D Systems, β-Secretase Activity Kit, Catalog No. FP002, Aug. 2002, 2 pgs.

Roberds et al., "BACE knockout mice are healthy despite lacking the primary β-secretase activity in brain: implications for Alzheimer's disease therapeutics," Human Molecular Genetics, Jun. 2001; 10(12): 1317-1324.

Ryu, Biomaterials 26: 319-326 (2005).

Salehi et al., J. Neural Transm. 106 955-986 (1999).

Sapru et al., Annual Meeting Soc. Neurosci. Abstract 297.9, XP001204566 (2003).

Sarver et al., Science 247, 1222-1225 (1990).

Scanlon et al., Proc. Nat. Acad. Sci. 88, 10591-10595 (1995).

Schenk, "Amyloid-β immunotherapy for Alzheimer's disease: the end of the beginning," Nature Reviews—Neuroscience, Oct. 2002; 3: 824-828.

Scherr et al., Cell Cycle 2(3) 251-257 (2003).

Serra et at., Medical Image Analysis 1(4) 317-329 (1996).

Singer et al., Nat. Neurosci. 8(10) 1343-1349 (ePub Aug. 28, 2005).

Stackman et al., Experimental Neurology 184, 510-520 (2003).

Strategene, AAV Helper-Free System, Instruction Manual, Catalog #240071, #240074, #240075, Revision #084007i, Aug. 2004, 50 pgs.

Strategene, pBluescript® II Phagemid Vectors, Instruction Manual, Catalog #212205, #212206, #212207, #212208, Revision #083001m, Aug. 2003, 35 pgs.

Sullenger, Science 262, p. 1566 (Dec. 3, 1993).

Taira et al., Nucl. Acid. Res. 19(19) 5125-5130 (1991).

Thompson et al., Nucl. Acid. Res. 23(12), 2259 (1995).

Timson et al., Biochem J 363:515-520 (2002).

Tuscjl Lab, "The siRNA user guide," Revised May 2004, [online]. Retrieved on Nov. 29, 2005. Retrieved from the Internet: <URL:rockefeller.edu/labheads/tuschl/sirna.html>; 6 pgs.

Valbonesi et al., Ttransf. And Apheresis Sci. 30: 153-156 (2004).

Van Bilsen et al., "Identification and allele-specific silencing of the mutant huntingtin allele in Huntington's disease patient-derived fibroblasts," Human Gene Therapy, vol. 19, pp. 710-718 (2008).

Vassar et al., Science 286 735-741 (1999).

Ventura et al., Nucl. Acid. Res. 21(14) 3249-3255 (1993).

Vickers, Journal of Bio. Chemistry, vol. 278, No. 9 7108-7118 (2003).

Watanabe et al., J. Mol. Cel. Card. 37 (3) 691-698 (2004).

Weerasinghe et al., J. Virol. 65(10), 5531-3334 (1991).

Whitesell et al., Proc. Nat. Acad. Sci. 90: 4665-4669 (1993).

Xia et al., Nat. Biotech. 20, 1006-1010 (2002).

Xia et al., Nat. Med. 10(8) 816-820 (2002).

Yamamoto et al., Cell 101, 57-66 (2000).

Yu et al., Proc. Nat. Acad. Sci. 90 6340-6344 (1993).

Yu et al., Proc. Nat. Acad. Sci. 99 6047-6052 (2002).

Zhang et al., "Global Non-Viral Gene Transfer to the Primate Brain Following Intravenous Administration," Molecular Therapy, Jan. 2003; 7(1): 11-18.

Zhang et al., "In vivo knockdown of gene expression in brain cancer with intravenous RNAi in adult rats," J. Gene Med., 2003; 5:1039-1045; published online Aug. 4, 2003.

Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.

Zhang et al., 1996 J. Mol. Neurosci. 7: 13-28 (1996).

Zhao et al., J. Biol. Chem. 271(49), 31407-31411 (Dec. 1996).

Zlokovic et al., Neurosurgery 40 805-813 (1997).

* cited by examiner

CHRONICALLY IMPLANTABLE GUIDE TUBE FOR REPEATED INTERMITTENT DELIVERY OF MATERIALS OR FLUIDS TO TARGETED TISSUE SITES

FIELD OF THE INVENTION

The present invention relates to a chronically implantable guide tube. More particularly, the present invention discloses a chronically implantable guide tube designed to provide recurrent controlled delivery of a chemical or pharmaceutical substance without the need for repeated stereotactic neurosurgery or additional stereotactic apparatuses.

BACKGROUND OF THE INVENTION

Generally, to administer certain types of pharmaceutical therapies to a neurological site, surgeons must perform repeated neurosurgeries. Specifically, the neurosurgeon must repeatedly localize the desired target site in the brain using stereotactic procedures. Stereotactic surgery is achieved by attaching a light weight metal superstructure to the patient's head to provide a fixed frame of reference for insertion of electrodes, probes, instruments or other medical devices into the brain. The apparatus provides multiple degrees of freedom in space for adjusting the positioning of the medical device to be inserted into the brain. Therefore as the patient's head moves in space the metal superstructure also moves in a one to one correspondence. However, the electrode, probe or device to be inserted into the patient's brain is immobilized with respect to the superstructure and therefore always remains in the same position relative to the head or brain. Hence, the stereotactic frame serves as a platform whereby an instrument is guided to a desired brain target site using stereotactic coordinates. That is, pre-mapped brain coordinates are used that are set on the superstructure. The positioning of the target site with respect to the metal frame is verified with imaging techniques, such as CT or MRI images. From this known relationship, the stereotactic coordinates are determined for positioning the probe in the target site. In addition, other techniques are also used to verify the target site area, such as using stimulation or recording electrodes. For example, the target site or nearby adjacent areas can be stimulated with a stimulation electrode for determining appropriate neurophysiological responses. In other situations, a recording electrode can be used to sample neuronal activity to confirm target site location. Once the instrument is guided to the desired target, treatment can begin, such as the administration of a biologic, chemical or pharmaceutical substance to the target site.

The above techniques and procedures are used for each surgical operation. However, repeated intermittent application of pharmaceutical agents to the same target site over time (such as days, weeks, months, etc.) would require many neurosurgical operations. Besides the known risks of multiple repeated operations, there are a number of other difficulties and risks to the patient. Repeated neurosurgical procedures can result in sub-optimal placement of the instrument with respect to the target site that may lead to significant morbidities or failure of the treatment. Sub-optimal placement may result from brain shifts during the operative procedure, changes in tissue pressure or consistency with repeated penetrations of the instrument, deflection of the instrument as it passes through previously penetrated brain tissue to the desired target or may result from miscalculation of stereotactic coordinates.

Additionally, repeated stereotactic neurosurgery may result in damage to the target site. Damage to a target site or region of interest is harmful to the patient's brain tissue and may necessitate a relocation of the target point. Hence, delivery of a biologic, chemical, or pharmaceutical without the need for repeated stereotactic neurosurgery or additional stereotactic apparatuses is greatly desired for such therapies.

Another problem associated with current devices is the delivery of pharmaceuticals to patients that may over-extend the target area. Over-extension and into and beyond the target site may cause damage to the patient's surrounding brain tissue and potentially cause a corresponding functional loss. Therefore, a delivery system that precisely targets the area of interest without over-extending the delivery site is important for patient safety.

Several prior art apparatuses allow for the introduction of drugs or therapeutic agents to selected brain tissue sites. U.S. Patent Application Publication No. 2004/0215164 A1 discloses a catheter assembly for intracranial treatments. This device is not chronically implantable, nor does this device prevent over-extension into the delivery site. Tissue or fluid accumulation at the target area can interfere with precise delivery of pre-determined amounts of substances. Another prior art device is described in U.S. Pat. No. 5,800,390. This patent discloses an intracranial tube for delivery of a pharmaceutical. Similarly, this device also does not prevent overshooting or over-extension into the delivery site.

Another prior art device is described in U.S. Patent Application Publication No. 2004/0186422. This application discloses an apparatus for delivering therapeutic or diagnostic agents to a target site within tissue. However, this device is also not chronically implantable, nor does this device prevent over-extension into the delivery site.

It is therefore desirable to provide a therapy delivery system that is chronically implantable to prevent damage to the target site for intermittent repeated surgeries, and which also prevents overshooting or over-extension into the delivery site.

SUMMARY OF THE INVENTION

The present invention relates to a chronically implantable guide tube for use in neurosurgery. The device is particularly useful in delivering a pharmaceutical to a stereotactically targeted surgical site for the treatment of abnormalities of brain function. These abnormalities may include movement disorders such as Parkinson's disease, chorea, tremor, multiple sclerosis, and cerebral palsy. Treatment for abnormalities of the mind may include depression, obsessive compulsive states, Alzheimer's disease, chronic pain syndromes and epilepsy. The device can also be used in the targeted treatment of brain tumors. In general the invention can be used to treat multiple neurological disorders or diseases, including enzyme deficiencies (e.g., lysosomal storage disorders), and stroke. Specifically, this device can be used to administer viral vectors and vectorless nucleic acid sequences for gene therapy and for protein suppression therapies.

The invention is particularly useful for the delivery of biologic, chemical, or pharmaceutical materials to a targeted area with an intermittent release protocol. The invention supports treatment protocols with variant dosing intervals, such as hours, days, weeks, months or variations thereof.

One aspect of the invention discloses a chronically implantable guide tube to provide delivery of a pharmaceutical without the need for repeated stereotactic neurosurgery. The chronically implantable guide tube includes a guide cannula, an access port mounted on a proximal end of the guide cannula, and a first stop disposed near the distal end of the guide cannula. When inserted into the guide tube, the relative positions of the first stop on the guide cannula, and a second stop on a delivery cannula prevent the delivery cannula from extending beyond a predetermined distance from the distal end of the guide tube. The first stop can also be disposed on a distal region of the guide tube, that is, the lower half or lower third regions. With the second stop appropriately positioned, the delivery cannula would then be advanced at a predetermined distance. However, the preferred embodiment is to dispose the first stop at the distal end of the guide tube with the appropriate positioning of the second stop on the delivery cannula.

In one embodiment, a tissue-piercing tip is attached to the distal end of the delivery cannula that is to be guided down the guide tube into a target site in the patient. The tissue-piercing tip can be used to penetrate any tissue plug or clot at the distal end of the chronically implantable guide tube that may otherwise block the flow of a substance or pharmaceutical from the delivery cannula into the tissue.

In certain embodiments, a stylet is inserted in the lumen of the chronically implantable guide tube to plug the distal region of the guide tube. The stylet may plug the chronically implantable guide tube during chronic periods between deliveries of various biologics, chemicals or pharmaceuticals during different therapies. In certain embodiments, the stylet may include a pharmaceutical or other substance to maintain patency.

BRIEF DESCRIPTION OF THE DRAWINGS

The drawings illustrate the design and utility of preferred embodiments of the present invention. In order to better appreciate how the advantages and objects of the present inventions are obtained, a more particular description of the present inventions in reference to specific embodiments are illustrated in the accompanying drawings. With the understanding that these drawings depict only typical embodiments of the invention and are not intended to limit its scope, the invention will be described and explained with additional specificity and detail through the use of the accompanying drawings.

DETAILED DESCRIPTION

Figures 1, 2, 3:
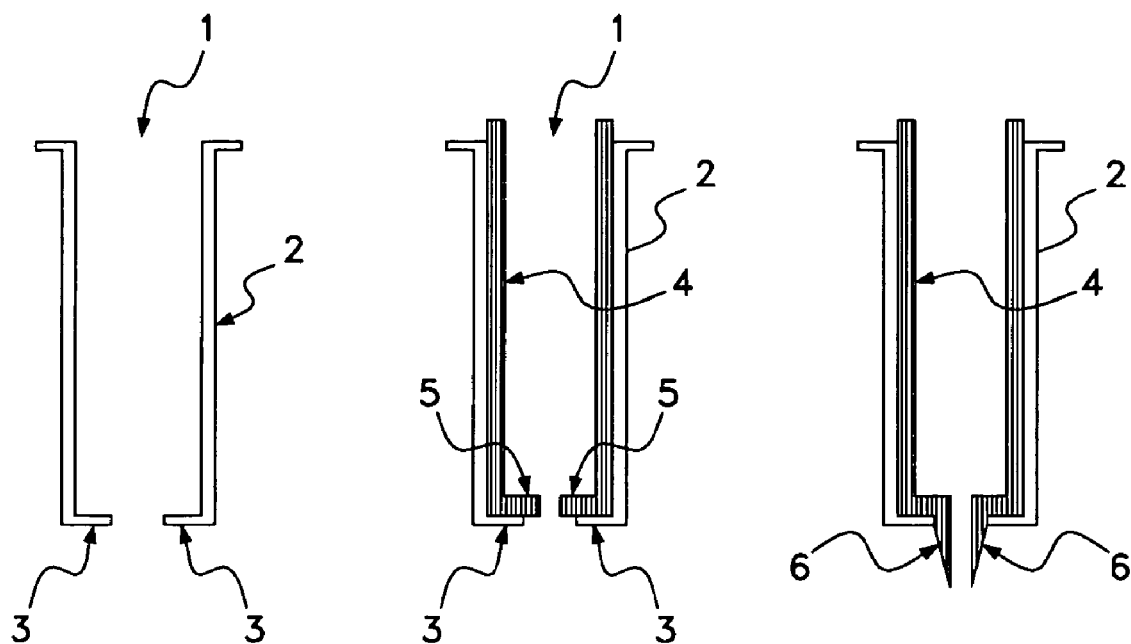
FIG. 1 is a cross-sectional side view along the longitudinal axis of a chronically implantable guide tube.
FIG. 2 is a cross-sectional side view along the longitudinal axis of a chronically implantable guide tube with a delivery cannula inserted within the guide tube.
FIG. 3 is a cross-sectional side view along the longitudinal axis of a one embodiment of the chronically implantable guide tube with a delivery cannula inserted within the guide tube having a tissue-piercing tip.

A first embodiment of the chronically implantable guide tube is depicted in FIG. 1. The chronically implantable guide tube 2 has an access port 1, and a first stop 3. The chronically implantable guide tube 2 is designed to provide for the administration of a biologic, chemical or pharmaceutical substance to a patient in need thereof. A pharmaceutical therapy may be, for example, a viral vector for gene-based therapies, a composition of biodegradable polymer microspheres encapsulating a pharmaceutical agent, including compounds of both proteinaceous and non-proteinaceous nature, a composition comprising DNA along with a polymeric carrier molecule for the treatment of neurodegenerative diseases, cells, including, without limitation stem cells from autologous or allogenic source, or genetically modified cells, or any other suitable pharmaceutical agent.

The chronically implantable guide tube 2 depicted in FIG. 1 may be fabricated from a variety of materials, such as plastics, polymers, metals, alloys, graphite and/or composites of such materials.

In certain embodiments, the chronically implantable guide tube comprises a first radiopaque marker selected for high visibility during fluoroscopy. In this embodiment, the radiopaque marker is positioned around the distal end of the guide tube 2. The radiopaque marker allows imaging of the distal end of the guide tube 2 during surgery to assess the positioning of the distal end 2 with respect to the intended target site 12. Radiopaque markers may also be used along the length of the guide tube for fluoroscopic or x-ray confirmation of the trajectory of the tube within the patient's brain.

The first stop 3 in the chronically implanted guide tube is a flange that prevents a delivery cannula, depicted in FIG. 2 and described below, from extending into the patient's brain tissue 13 past a predetermined target site 12.

One embodiment of the guide tube is depicted in FIG. 2. This embodiment includes a delivery cannula 4 inserted into the guide tube 2 through the access port 1. The cannula has a second stop 5 adapted to mechanically interact with the first stop 3 of the guide tube. The delivery cannula 4 is slidable within the guide tube 2.

Any of the materials discussed previously with reference to the chronically implantable guide tube may also be suitable for the construction of the delivery cannula. A highly flexible delivery cannula is desirable, as it cannot then be forced past the first stop in the guide cannula. The delivery cannula may be a single use cannula to reduce the risk of infections, and may utilize radiopaque materials or markers for fluoroscopic control of its trajectory inside the guide tube.

In other embodiments, the delivery cannula comprises a second radiopaque marker for fluoroscopic or x-ray visualization of the tip of the cannula. Multiple radiopaque markers may also be used on the length of the delivery cannula for confirmation of its trajectory relative to the patient's neural tissue.

It is understood by those skilled in the art that the flexibility or stiffness of the invention may be varied by using different materials or combination of materials for the chronically implantable guide tube and the delivery cannula.

Figure 10:
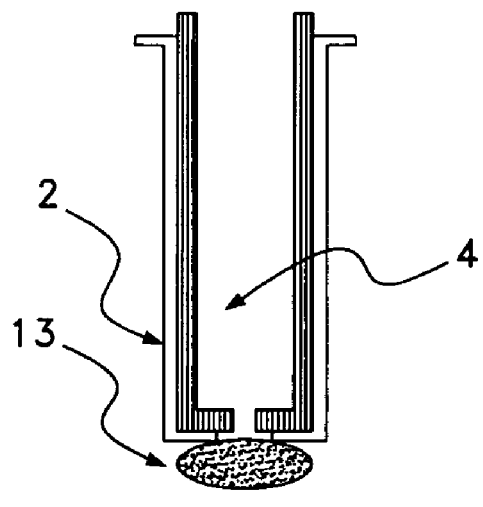
FIG. 10 is a cross-sectional side view along the longitudinal axis of a chronically implantable guide tube with a delivery cannula inserted within the guide tube showing a blood clot or tissue mass at the distal end of the implantable guide tube.
Figure 11:
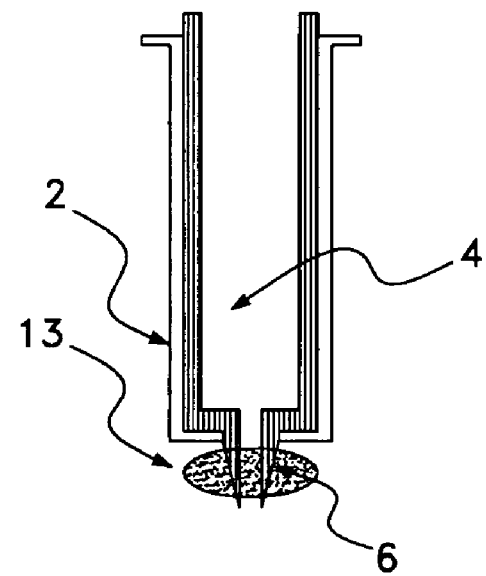
FIG. 11 is a cross-sectional side view along the longitudinal axis of a chronically implantable guide tube with a delivery cannula inserted within the guide tube having a tissue-piercing tip penetrating a blood clot or tissue mass at the distal end of the guide tube.

Yet another embodiment of the chronically implantable guide tube is depicted in FIG. 3. In FIG. 3, the tissue-piercing tip 6 is attached to the end of the cannula inserted into the guide tube. FIG. 10 illustrates a blood clot or tissue mass 13 attached to the distal end of the implanted guide tube 2 with a delivery cannula 4 inserted within the guide tube. Delivery of a pharmaceutical agent through the use of the delivery cannula 4 in FIG. 10 could be compromised as a result of a blood clot. However, FIG. 11 illustrates that the tissue piercing tip 6 can be used to penetrate the blood clot or tissue mass 13 and to allow the effective delivery of an appropriate substance, such as a pharmaceutical, through the delivery cannula attached to the tissue-piercing tip.

Figures 4, 5:
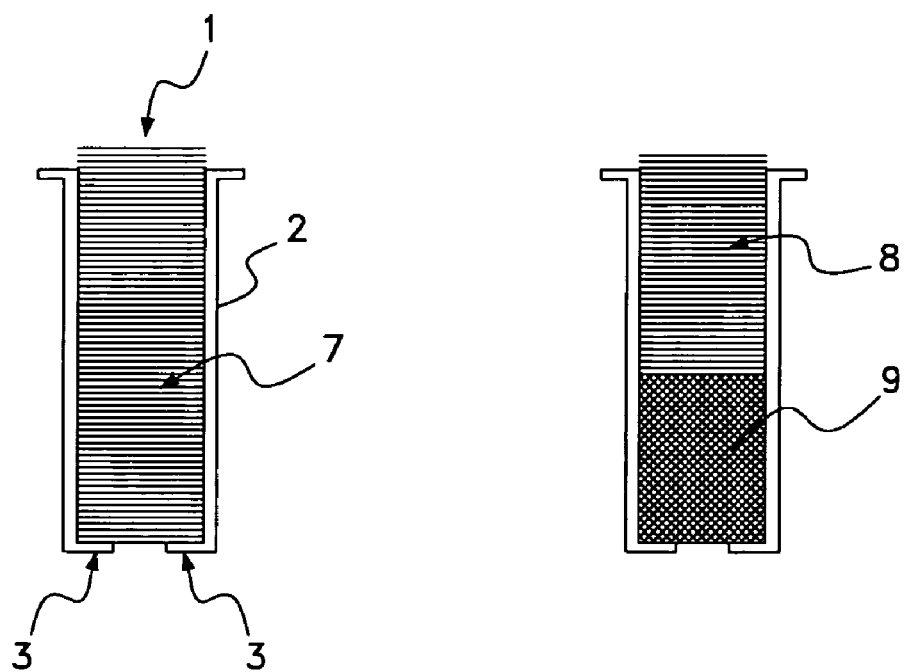
FIG. 4 is a cross-sectional side view along the longitudinal axis of the chronically implantable guide tube showing one embodiment of a stylet inserted within the guide tube.
FIG. 5 is a cross-sectional side view along the longitudinal axis of the chronically implantable guide tube of another embodiment of the stylet having a distal end formed from a tissue-compatible material and a proximate end having an antibacterial region.
Figures 6, 7A:
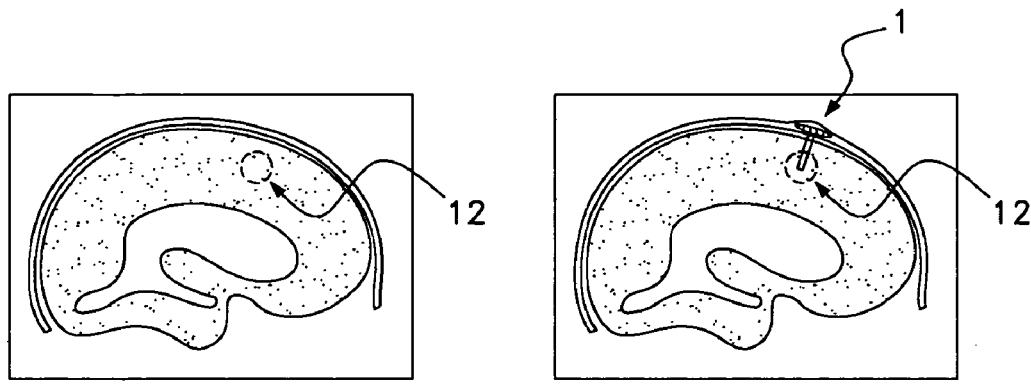
FIG. 6 is a sagittal view of a human skull and brain illustrating the target site of interest for pharmaceutical delivery of substances.
FIG. 7A is a sagittal view of a human skull and brain with the chronically implantable guide tube with a delivery cannula inserted within the guide tube having a tissue-piercing tip inserted into the brain tissue.
Figure 7B:
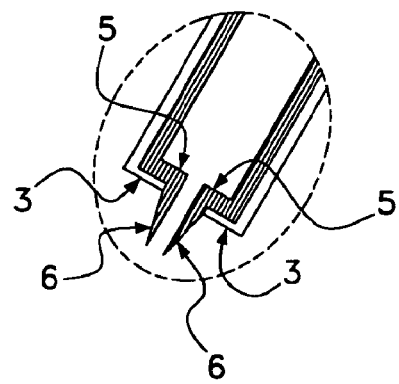
FIG. 7B is an enlargement of the details of the distal end of the chronically implantable guide tube with delivery cannula from the area shown by the dotted lines in FIG. 7A.
Figures 8, 9:
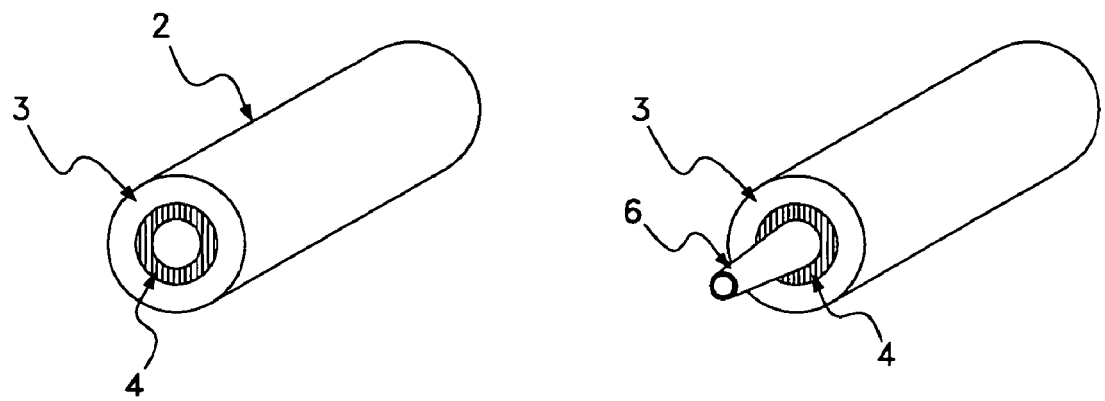
FIG. 8 is a three dimensional view of the chronically implantable guide tube with a delivery cannula inserted within the guide tube.
FIG. 9 is a three dimensional view of the chronically implantable guide tube with a delivery cannula inserted within the guide tube having a tissue-piercing tip.

Still another embodiment of the chronically implantable guide tube is depicted in FIG. 4. In FIG. 4, a stylet 7 is inserted into the guide tube to plug the distal region of the guide tube. The stylet 7 is also flexible and compliant so as not to go beyond the first stop of the guide tube. The stylet may be coated with chemicals exhibiting antibiotic, antibacterial, or antimicrobial properties. For example, the chemical coating may comprise copper silicate, silver silica, colloidal silver, or alkylated polyethyleneimine or any combinations of such materials. Further, the stylet may be fabricated, impregnated or formed from materials comprising copper silicate, silver silica, colloidal silver, or alkylated polyethyleneimine or any combinations of such materials. The stylet may also be formed from other materials known in the art that are tissue compatible or non-toxic, but exhibit antibacterial, or antimicrobial properties. Additionally, the stylet may be coated with one or more pharmaceuticals, comprising substances useful for inhibiting inflammation, preventing ingrowth of the tissue into the cavity of the guide tube, substances preventing cell attachment, or substances effective in maintaining the guide tube pathogen-free (e.g., antibiotics).

The stylet is inserted into the access port 1 of the guide tube 2 and is slidable. Because the stylet 7 mechanically interacts with the first stop of the guide tube 3, the stylet cannot extend past the distal end of the guide tube. The stylet may be inserted into the guide tube to prevent tissue in-growth and fluid accumulation between therapeutic administrations. Further, it reduces the risks of potential infections to the patient and maintains an unobstructed pathway for the insertion of the delivery cannula.

The therapy delivery system of the instant invention may further comprise anchoring means to keep the stylet from moving in and out of the guide cannula between treatments. A person of the ordinary skill in the art will appreciate that a variety of ways exist to achieve this objective. In one embodiment, the stylet and the guide cannula may be in a threaded arrangement, so the stylet is screwed into the guide cannula. In another embodiment, there may be a notch in the stylet or the guide cannula, and a corresponding groove in the guide cannula or the stylet. The groove may further comprise a change in geometry so that the stylet cannot be removed with a single longitudinal movement (e.g., without twisting the stylet in the guide cannula. In yet another embodiment, the access port may comprise a lid or a cap which would prevent the stylet from sliding in and out of the guide cannula. The combination of these arrangements is also envisioned.

Depicted in FIG. 5 is another embodiment of the stylet having a distal end 9 formed from a tissue-compatible material (e.g., a material which is not toxic at physiological conditions and degradation of which at physiological conditions does not result in toxic residues) and a proximate 8 end formed with tissue-compatible material having antibacterial properties. For example, and without limitation, the tissue-compatible material having antibacterial properties may be an antibiotic-impregnated cement comprised of tobramycin and bone cement as has been used in the formation of nails for orthopedic applications, as described in Madanagopal, S. G., Seligson, D. & Roberts, C. S. The antibiotic cement nail for infection after tibial nailing. *Orthopedics* 27, 709-712 (2004). Alternatively, the tissue-compatible material having antibacterial properties may be platinum black or silver powder, as disclosed by Sanrangapani in WO199805461.

In yet another embodiment, the delivery cannula interfaces with a microsyringe comprising a catheter for insertion into the guide tube, a flow regulator through which the biologic, chemical or pharmaceutical agent is release at a predetermined rate, a delivery chamber containing a predetermined amount of fluid volume and biologic, chemical or pharmaceutical agent to be injected into the brain tissue, and a second chamber (separate from the first chamber) containing a septum that acts as a piston or plunger to deliver the material through the catheter. The second chamber may be filled with hydraulic fluid, oil, gas, air or other suitable substance to provide controlled pressures for releasing the biologic, chemical or pharmaceutical agent into the brain tissue. A non-limiting example of a suitable microsyringe has been disclosed, for example, in a co-pending application Ser. No. 11/562,282, (Kaemmerer) filed Nov. 21, 2006.

Still yet another embodiment of the invention, the guide tube may also be implanted in the cerebral ventricles for therapeutic delivery of the substance into the cerebral spinal fluid of the patient. Intermittent, acute and invasive delivery of a slurry of small solids, for example, polymer and drug pellets, can be introduced into the cerebral spinal fluid of the cerebral ventricles. The invention may also be used for the intermittent delivery of biologic, enzyme, chemical or pharmaceutical materials in cardiac infarct sites, pancreas or other tissues. The invention can provide a system for intermittent acute delivery of materials for the transplant of islet cells in the pancreas. In another embodiment, the invention provides a system for delivery of cardiomyocytes to the infarcted areas of myocardium.

The invention includes a therapy delivery method comprising (a) implanting a guide tube within a patient, a distal section of the guide tube comprising a first stop; (b) inserting into a proximal end of the guide tube a first delivery cannula, the first delivery cannula having a second stop; (c) feeding the first delivery cannula into the guide tube until the first stop contacts the second stop; (d) delivering a first pharmaceutical into the first delivery cannula; and (e) extracting the first delivery cannula. For example, a first delivery of a first pharmaceutical to a patient using the subject invention could consist of delivering through the guide tube into the brain tissue of the patient a dose of adeno-associated viral (AAV) vector containing approximately $150 \times 10^9$ viral particles in a volume of 50 to 150 microliters of fluid, where the AAV vector contains DNA encoding for a therapeutic gene product. The DNA encoding for the therapeutic gene product may incorporate DNA sequences designed to be recognized by a DNA recombinase such that future contacting of the brain tissue treated with the AAV-delivered DNA by the DNA recombinase would silence the expression of the therapeutic gene product. Thus, using the subject invention, the gene therapy delivered to the patient at one point in time could optionally be reversed at a future point in time if necessary, with the chronically implanted guide tube of the subject invention ensuring that the DNA recombinase needed to reverse the gene therapy is delivered to the same tissue location as that to which the gene therapy was delivered at the first point in time.

In certain embodiments of the therapy delivery method the stylet is (a) extracted from the guide tube; (b) a second delivery cannula, having a third stop, is inserted into the proximal end of the guide tube; (c) the second delivery cannula is fed into the guide tube until the first stop contacts the third stop; (d) a second pharmaceutical, that may be the same as the first pharmaceutical, is delivered; and (e) the second delivery cannula is extracted. For example, a first delivery of a first pharmaceutical to a patient using the subject invention could consist of delivering through the guide tube into the brain tissue of the patient a dose of adeno-associated viral (AAV) vector containing approximately 150×10 viral particles in a volume of 50 to 150 microliters of fluid, where the AAV vector contains DNA encoding for a therapeutic gene product and the AAV serotype is serotype 1. Next, at a later point in time if additional gene therapy is required for the patient, a second delivery of a second pharmaceutical to the patient using the subject invention could consist of delivering through the guide tube into the brain tissue of the patient a dose of adeno-associated viral (AAV) vector containing approximately $150 \times 10^9$ viral particles in a volume of 50 to 150 microliters of fluid, where the AAV vector contains DNA encoding for a therapeutic gene product and the AAV serotype is serotype 1, or optionally, a different serotype than serotype 1. The use of a different serotype than serotype 1 for the second administration of the therapy to the patient may be beneficial in terms of maximizing the therapeutic efficacy of the second administration if the patient's immune system has developed neutralizing antibodies to the proteins of AAV serotype 1.

In some applications of the method of the instant invention, a precise placement of the guide cannula is crucial. A non-limiting example of such application is the use of the method for treating disorders of the brain. Thus, the practitioner (e.g., a person who uses the system and the method of the instant invention) should select the suitable mapping means. Suitable mapping means are known in the art. Such mapping means include, without limitation, Positron Emission Tomography and Single Photon Emission Computed Tomography (PET and SPECT, respectively), pharmacological Magnetic Resonance Imaging (phMRI), functional MRI (fMRI), and contrast-enhanced computerized tomography (CT) scan.

Further, computer-aided atlas-based functional neurosurgery methodology can be used to accurately and precisely place the guide cannula of the present invention. Such methodologies permit three-dimensional display and real-time manipulation of cerebral structures. Neurosurgical planning with mutually preregistered multiple brain atlases in all three orthogonal orientations is therefore possible and permits increased accuracy of target definition for treatment injection or implantation, reduced time of the surgical procedure by decreasing the number of tracts, and facilitates planning of more sophisticated trajectories. See e.g. Nowinski W. L. et al., Computer-Aided Stereotactic Functional Neurosurgery Enhanced by the Use of the Multiple Brain Atlas Database, IEEE Trans Med Imaging 19(1); 62-69:2000.

For example, Serra et al. (the teachings of which are incorporated herein by reference in its entirety) describe technological improvements for surgery in human brains, comprising the use of ST and MR imaging, and the incorporation of detailed stereotactic atlases compiled over the years into their system of hardware and software for planning and carrying out neurosurgery. For example, Serra et al. describe an "electronic brain atlas" for identifying brain targets. Serra et al. describe the use of their system to target brain structures with almost any art-recognized surgical instrument, including probes and delivery devices. Further, Serra et al. provide a detailed blueprint and disclose devices and software, and refer to several print publications, describing, teaching, and showing the use of stereotactic atlases to identify and locate virtually any target in the human brain.

One of skill interested in particular region of the human brain, may, in addition to referring to Serra et al., use the teachings of Morel et al., among others, who disclose a detailed atlas of human thalamus. Morel et al. discuss that computer tomography and magnetic resonance imaging-guided stereotaxy and preoperative microelectrode recordings for localization of targets has aided stereotactic neurosurgery.

Further, in 2001, Medtronic introduced a "mapping means" device termed the Medtronic NT StealthStation® Treon™ into the marketplace. This medical system further refines the computerized technologies of multi-dimensional imaging and navigation to enable neurosurgeons to precisely plan, re-plan and visualize a procedure as it proceeds deep within the brain for treating neurological disorders in a living human patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A therapy delivery system comprising:
   a chronically implantable guide tube comprising:
   a guide cannula having a proximal end and a distal end;
   an access port mounted on the proximal end of the guide cannula and adapted for chronic implantation into a patient; and
   a first stop mounted near the distal end of the guide cannula, wherein the first stop is closer to the distal end than the proximal end; and
   a delivery cannula insertable into the guide cannula through the access port, the delivery cannula comprising a second stop adapted to mechanically interact with the first stop;
   wherein the relative positions of the first stop and the second stop prevent a distal end of the delivery cannula from distally extending beyond a predetermined distance from the distal end of the guide cannula.

2. The therapy delivery system of claim 1, wherein the distal end of the delivery cannula comprises a tissue-piercing tip.

3. The therapy delivery system of claim 1, wherein the first stop comprises a flange.

4. The therapy delivery system of claim 3, wherein the flange is disposed at the distal end of the guide cannula.

5. The therapy delivery system of claim 1 further comprising a stylet insertable into the guide cannula, the stylet adapted to plug at least a distal region of the guide cannula.

6. The therapy delivery system of claim 5, wherein the stylet comprises a chemical having antibiotic, antibacterial, or antimicrobial properties.

7. The therapy delivery system of claim 6, wherein the chemical comprises a pharmaceutical agent comprising an antibiotic, or an anti-inflammatory.

8. The therapy delivery system of claim 6, wherein the chemical comprises an antibacterial or an antimicrobial agent comprising copper silicate, silver silica, colloidal silver, platinum black, tobramycin and bone cement, or alkylated polyethyleneimine or any combinations thereof.

9. The therapy delivery system of claim 5, wherein the stylet consists of tissue-compatible materials, and wherein a distal end and a proximate end of the stylet are formed of different tissue-compatible materials.

10. The therapy delivery system of claim 9, wherein the distal end of the stylet is formed of a tissue-compatible material and the proximate end with a tissue-compatible material having antibacterial properties.

11. The therapy delivery system of claim 1, wherein the guide cannula comprises a first radiopaque marker.

12. The therapy delivery system of claim 11, wherein the first radiopaque marker is disposed on the distal end of the guide cannula.

13. The therapy delivery system of claim 11, further comprising a plurality of the first radiopaque marker disposed along the length of the guide cannula for fluoroscopic or X-ray confirmation of the guide cannula trajectory.

14. The therapy delivery system of claim 1, wherein the delivery cannula is formed from a flexible material to prevent advancement beyond the first stop mounted on the distal end of the guide cannula.

15. The therapy delivery system of claim 1, wherein the delivery cannula comprises a second radiopaque marker.

16. The therapy delivery system of claim 15, wherein the second radiopaque marker is disposed on the distal end of the delivery cannula.

17. The therapy delivery system of claim 15, further comprising a plurality of the second radiopaque markers disposed along the length of the delivery cannula for fluoroscopic or X-ray confirmation of the delivery cannula trajectory.

18. A therapy delivery method comprising:
    implanting a guide tube within a patient, a distal section of the guide tube comprising a first stop, a proximal end of the guide tube comprising an access port, wherein the first stop is closer to a distal end of the guide tube than to the proximal end;
    inserting into the proximal end of the guide tube a first delivery cannula, the first delivery cannula having a second stop;
    feeding the first delivery cannula into the guide tube until the first stop contacts the second stop;
    delivering a pharmaceutical into the first delivery cannula; and
    extracting the first delivery cannula.

19. The therapy delivery method of claim 18 further comprising inserting into the guide tube a stylet after extracting the first delivery cannula, the stylet adapted to plug a distal end of the guide tube.

20. The therapy delivery method of claim 19 further comprising:
    extracting the stylet from the guide tube;
    inserting into the proximal end of the guide tube a second delivery cannula, the second delivery cannula having a third stop;
    feeding the second delivery cannula into the guide tube until the first stop contacts the third stop;
    delivering a second pharmaceutical into the second delivery cannula; and
    extracting the second delivery cannula.

21. The therapy delivery method of claim 18, wherein the guide tube is implanted within a brain of the patient.

22. The therapy delivery method of claim 21, further comprising locating a pre-determined location within the brain using a mapping means.

23. The therapy delivery method of claim 18 wherein said pharmaceutical is selected from the group consisting of bioactive drugs, viral vectors, and proteins.

* * * * *